United States Patent [19]

Schirmann

[11] 4,338,260

[45] Jul. 6, 1982

[54] PREPARATION OF PERCARBOXYLIC ACIDS

[75] Inventor: Jean-Pierre Schirmann, Oullins, France

[73] Assignee: PCUK Produits Chimiques Ugine Kuhlmann, Courbevoie, France

[21] Appl. No.: 181,830

[22] Filed: Aug. 27, 1980

[30] Foreign Application Priority Data

Sep. 7, 1979 [FR] France .................................. 79 22398

[51] Int. Cl.$^3$ .......................................... C07C 179/10
[52] U.S. Cl. ............................................... 260/502 R
[58] Field of Search ......................... 260/502 R, 502 A

[56] References Cited

U.S. PATENT DOCUMENTS 2,806,045 9/1957 Gross ............................. 260/502 R
2,814,641 11/1957 Phillips et al. ................... 260/502 R
2,877,266 3/1959 Korach ............................ 260/502 R
4,059,619 11/1977 Prescher et al. ................. 260/502 R

FOREIGN PATENT DOCUMENTS 1492059 7/1967 France .

OTHER PUBLICATIONS

Swern, "Organic Peroxides", Wiley Interscience (pub.), (1970), vol. 1, pp. 313–369 and 426–439.

*Primary Examiner*—Werren B. Lone
*Attorney, Agent, or Firm*—Pennie & Edmonds

[57] ABSTRACT

A process for the preparation of percarboxylic acids by the action of hydrogen peroxide on water miscible carboxylic acids in the presence of a boric acid catalyst and a solvent capable of forming a heteroazeotrope with the water and continuously eliminating the water which may have been added with the hydrogen peroxide and the water formed during the reaction by azeotropic distillation.

9 Claims, No Drawings

PREPARATION OF PERCARBOXYLIC ACIDS

TECHNICAL FIELD

The invention relates to a process for the preparation of percarboxylic acids from water-miscible aliphatic carboxylic acids and hydrogen peroxide. The reaction is carried out in the presence of a catalytic quantity of ortho- or metaboric acid and an azeotropic entraining solvent whereby water is eliminated continuously from the reaction medium by distillation.

BACKGROUND ART

It has been known for a long time (Ber. 45, 1845, 1912) that hydrogen peroxide reacts with aliphatic carboxylic acids to form percarboxylic acids according to the following reaction:

$$R-\underset{\underset{O}{\|}}{C}-OH + H_2O_2 \rightleftharpoons R-\underset{\underset{O}{\|}}{C}-O-OH + H_2O \quad (1)$$

It is also known (D. Swern, ORGANIC PEROXIDES, Wiley Interscience, 1970, Vol. I) that although a few rare peracids, particularly performic acid, can be prepared in the absence of a catalyst, it is generally necessary for the majority of them to employ a catalyst to reduce the reaction time.

In fact, because of the instability of percarboxylic acids, this reaction is generally performed at a moderate temperature. Under these conditions, a state of equilibrium is not reached until after several hours of reaction time, and such a duration is not acceptable in an industrial process. Therefore, it is necessary to resort to the use of a catalyst.

The catalysts that have been proposed and used up to now are strong mineral or organic acids, such as phosphoric acid, sulfuric acid, hydrochloric acid, alkylor arylsulfonic acids, such as methanesulfonic acid, paratoluenesulfonic acid, trifluoroacetic acid, as well as acid cationic resins such as "Dowex 50" or "Amberlite IR-120" commercial resins.

This catalytic process had been the object of many studies (D. Swern, ORGANIC PEROXIDES, Wiley Interscience, 1970, Vol. I, pages 313-369 and pages 428-439). It has been shown that the first step of the reaction corresponds to the protonation of the carboxylic acid function resulting in the formation of an oxonium structure capable of reacting with $H_2O_2$ to lead to percarboxylic acid according to this scheme:

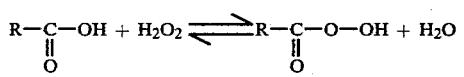

$$H_2O_2 \rightleftharpoons HOO^- + H^+ \quad (3)$$

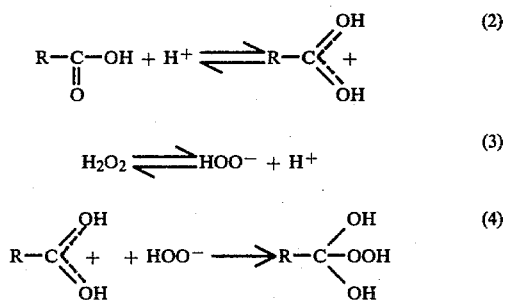

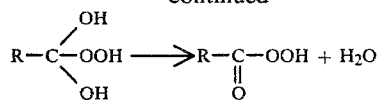

Hydrogen peroxide is most often employed in the form of commercial aqueous solutions containing 30 to 70% water. Since the reaction also supplies one molecule of water per molecule of percarboxylic acid, it is clear that the state of equilibrium (1) is reached well before the hydrogen peroxide is completely converted. Under these conditions, the reaction product is actually a mixture of carboxylic acid, hydrogen peroxide, percarboxylic acid, water and strong acid catalyst.

Many means have been proposed to shift the equilibrium to the right, in order to utilize the hydrogen peroxide as completely as possible or to obtain a peroxide free of some of the other constituents of the equilibrium, frequently troublesome for the use intended. In fact, although it is sometimes possible to use the mixture as is and to complete the conversion of the hydrogen peroxide in situ, during certain epoxidations for example, this simple process is often inadequate because of the side reactions that can be caused by the other constituents of the mixture, such as oxidation by the hydrogen peroxide, hydrolysis by the water, and harmful action of the strong acid catalyst.

Most of the methods described use known means of dehydration of the organic media. Thus, it has been proposed that the reaction be conducted in the presence of a strong acid catalyst and of a sufficient quantity of dehydrating agents to combine with the water that is present or formed during the reaction. But the agents advocated up to now are not entirely satisfactory and, in addition, produce problems of separation that are difficult to solve from a practical standpoint. Thus, in French Pat. No. 1,492,059, metaboric acid is proposed as a stoichiometric fixing agent for water, in the presence of strong acid catalysts. This method does make it possible to attain very high levels of conversion of the hydrogen peroxide, but necessitates separating the orthoboric acid resulting from the hydration of the metaboric acid and which is insoluble in the medium. The necessity of handling a solid that may be impregnated with peracid and then having it undergo dehydration at high temperature makes this process tricky and difficult to carry out.

It has also been proposed, as in U.S. Pat. No. 2,877,266 and No. 2,814,641, to operate only with a very slight excess of carboxylic acid, but in the presence of a strong mineral acid catalyst and an azeotropic entraining agent to eliminate the water and shift the equilibrium (1) to the right. Such a practice is indeed excellent with respect to the yield of percarboxylic acid in relation to the hydrogen peroxide involved.

However, all of these methods have a major drawback in common: while the solutions of peracids are being used, the strong acid catalyst needed to accelerate the reaction process most often produce parasitic reactions that result in significantly lower yields. It is well known, for example, that in reactions of epoxidation of olefins by peracids, the epoxide formed is easily opened and converted to a mixture of mono and diester under the effect of the strong acid catalysts.

It is true that the strong acid may be advantageously neutralized, but then the corresponding salt is generally insoluble in the medium and this poses problems of separation that are not unappreciable from a practical standpoint. Sometimes this salt is even as good a catalyst of parasitic reactions as the acid itself.

This is why, as in French Pat. No. 2,359,132 and No. 2,300,085, a two-stage manufacturing method for organic solutions of percarboxylic acids was proposed, which consists of allowing an aqueous solution containing from 10 to 45% sulfuric acid serving as a dehydrating agent and a catalyst and 20 to 35% hydrogen peroxide to react with propionic acid, and then extracting the perpropionic acid that has formed with a solvent such as benzene or dichloropropane. The aqueous phase must be concentrated to eliminate the water supplied by the hydrogen peroxide and the water formed during the reaction. The organic phase is washed with water to eliminate $H_2SO_4$, and then dried by azeotropic distillation. This solution does make it possible to obtain, with a good yield on the hydrogen peroxide, an organic solution of anhydrous perpropionic acid that has been rid of strong acid catalyst. However, this is a very cumbersome and therefore very costly method to use.

DISCLOSURE OF THE INVENTION

This invention involves a discovery that it is possible to achieve the same result, i.e., to obtain an anhydrous organic solution of percarboxylic acid free of all traces of strong mineral acid, by allowing carboxylic acid and hydrogen peroxide to react in the presence of catalytic quantities of orthoboric acid or metaboric acid and an azeotropic entraining solvent to permit the continuous elimination from the reaction medium of the water supplied by the aqueous solution of hydrogen peroxide as well as the water resulting from the reaction.

Orthoboric($H_3BO_3$) and metaboric $(HOBO)_n$ acids are well known to be weak mineral acids whose action as an acid cannot be compared with that of strong acids such as $H_2SO_4$. Therefore, this is without any doubt a different catalytic process, whose nature, however, is not yet known.

The carboxylic acids with which the invention is concerned are water-soluble aliphatic carboxylic acids, such as, formic, acetic, propionic and butyric acids.

The azeotropic entraining agent may be selected advantageously from among solvents with a boiling point of less than 100° C. and forming a heteroazeotrope with water. Solvents containing chlorine, such as chloroform, carbon tetrachloride, methylene chloride, dichloro-1,2 ethane, dichloropropane, solvents containing hydrocarbons, such as cyclohexane, benzene, toluene, esters, such as formiates, acetates, propionates, butyrates, isobutyrates of methyl, ethyl, propyl, isopropyl, n-butyl are some non-limiting examples.

The hydrogen peroxide which can be employed according to the invention can be in anhydrous form and in the form of a commercial aqueous solution with a titer of 30 to 70% by weight.

The process according to the invention therefore comprises reacting a carboxylic acid with hydrogen peroxide in the presence of the azeotropic entraining agent and the catalyst while continuously eliminating water from the reaction medium by azeotropic distillation.

The temperature at which the reaction is conducted ranges between 40° C. and 100° C. and preferentially between 40° C. and 70° C. Depending on the temperature selected and the reaction system employed, the elimination can be done by operating at atmospheric pressure or under reduced pressure. The pressure may therefore range between 20 mm of mercury and 760 mm of mercury.

The duration of the reaction depends on the nature of the catalyst, the nature of the carboxylic acid, the nature of the azeotropic entraining agent, and the temperature chosen. It may range from a few minutes to several hours. The reagents may be introduced in equimolecular quantities, but a molar excess or deficiency of one or the other of the reagents can also be utilized. As an indication, from 0.1 to 10 moles of carboxylic acid per mole of hydrogen peroxide can be used, but preferentially from 1 to 5 moles are used.

The catalyst is utilized in a quantity of 0.001 to 0.1 mole of boric acid per mole of hydrogen peroxide. However, the preferred molar ratio ranges between 0.001 and 0.01 mole per mole of hydrogen peroxide introduced.

The quantity of azeotropic entraining solvent ranges between 50 and 75% by weight of the reaction mixture, so that the boiling point of the mixture can be adjusted at will and the water can be eliminated efficiently.

The reagents can be used in their usual commercial form. Hydrogen peroxide in particular may be employed in the form of commercial aqueous solutions with a titer of 30% to 70% by weight. It may be advantageous to add to the reaction mixture products that stabilize hydrogen peroxide, such as phosphates, polyphosphates, derivatives of ethylenediaminetetraacetic acid, etc.

The solution of percarboxylic acid thus obtained can then serve for the oxidation of a very large number of organic compounds, such as olefins, ketones, amines, aromatic compounds, sulfur derivatives, etc., during a second operation. However, it is not always necessary to resort to this procedure and sometimes both operations, that is to say, the synthesis of the peracid and its immediate consumption by the molecule to be oxidized, can advantageously be performed at the same time. This constitutes a variant of the process according to the invention. Thus, when the organic compound which is intended to be oxidized by the carboxylic acid forms a heteroazeotrope with water, it may be used as an azeotropic entraining agent and, in the same step, react with the percarboxylic acid as the latter is formed. As an example, we can mention the epoxidation of cyclohexene or allyl chloride by peracetic acid or perpropionic acid. Such a procedure is particularly simple to demonstrate and offers great safety because it makes it possible to avoid any accumulation of peracid in the reaction medium.

In the context of this variant, if the compound to be oxidized does not form a heteroazeotrope with water, it is, of course, quite possible to operate in the presence of an azeotropic entraining solvent.

BEST MODES FOR CARRYING OUT THE INVENTION

The following examples are nonlimiting illustrations of the present invention:

EXAMPLES 1 to 7

In a 250-cm$^3$ reactor equipped with a distilling column of 5 Oldershaw plates with an overhead reflux condenser, place 50 g of propionic acid, 70 g of azeotropic entraining solvent, 0.2 g of catalyst (except in Examples 1 and 2 which are given for purposes of comparison) and 0.1 g of disodium phosphate. This mixture is made to reflux, and 0.1 mole of hydrogen peroxide in the form of an aqueous solution of 70% by weight is progressively introduced. The condenser is designed in such a way that only the condensed organic phase is refluxed in the column, while the decanted aqueous phase is drawn off continuously. The reaction conditions and the results are shown in Table I.

EXAMPLE 8 propylene. The temperature of the reactor is maintained at 50° C. The pressure in the reactor is 8 bars. At the outlet of the reactor, continuous decompression of the reaction mixture is conducted. The gas phase is washed with water in a washing column to recover the entrained propylene oxide. The liquid phase is cooled. An analysis of the reaction products shows that 0.01 mole of perpropionic acid comes out of the reactor and that 4 g/hr of propylene oxide has formed.

TABLE 1

| Examples | Carboxylic Acid | Catalyst | Solvent | T °C. | Pressure mm Hg | Duration min. | Remaining $H_2O_2$ in m moles | Peracids formed in m moles | Distilled $H_2O_2$ in m moles |
|---|---|---|---|---|---|---|---|---|---|
| 1 | Propionic | — | Cyclohexane | 93° | 760 | 30 | 14 | 12 | 35 |
| 2 | " | — | Dichloroethane | 50° | 150 | 180 | 20 | 5 | 3 |
| 3 | " | $H_3BO_3$ | Cyclohexane | 94° | 760 | 30 | 2 | 50 | 20 |
| 4 | " | " | Dichloroethane | 94° | 760 | 30 | 6 | 75 | 7 |
| 5 | " | " | " | 50° | 150 | 180 | 3 | 82 | 14 |
| 6 | " | $(HBO_2)_n$ | " | 50° | 150 | 180 | 3.9 | 90 | 5 |
| 7 | Acetic | $H_3BO_3$ | " | 50° | 180 | 180 | 7 | 87 | 6 |

In a 500-cm³ reactor equipped with a distillation column of 10 Oldershaw plates with an overhead reflux condenser of the same type as the one described above, place 125 g of propionic acid, 175 g of dichloro-1,2 ethane, 0.5 g of orthoboric acid $H_3BO_3$ and 0.1 g of disodium phosphate. Reflux is induced under a pressure of 150 mm of mercury. The temperature of the reaction medium is 50° C. Progressively add 0.3 mole of hydrogen peroxide in the form of an aqueous solution of 70% by weight. After two hours of reaction during which the water is eliminated continuously by azeotropic distillation, we find in the medium 0.24 mole of perpropionic acid as well as 0.027 mole of hydrogen peroxide, while the distilled aqueous phase contains 0.032 mole of hydrogen peroxide.

EXAMPLE 9

In a reactor such as described in Example 1, place 50 g of acetic acid, 80 g of allyl chloride as well as 0.2 g of orthoboric acid $H_3BO_3$. Induce a reflux and set the temperature at 55° C. Add 0.050 mole of hydrogen peroxide in the form of a 70% aqueous solution over a period of 15 minutes and continuously eliminate the water supplied by $H_2O_2$ and that formed during the reaction. After two hours of reaction, we find in the reaction medium 0.042 mole of epichlorohydrin, 0.002 mole of peracetic acid and 0.001 mole of hydrogen peroxide, while the distillate contains 0.004 mole of hydrogen peroxide.

EXAMPLE 10

In a tubular reactor 15 m in length and 2 mm in diameter, introduce continuously, after passage in a mixer, 100 g/hr of a solution of perpropionic acid prepared according to Example 8, with a titer of 6.7% of peracid and 0.15% of hydrogen peroxide, as well as 21 g/hr of

I claim:

1. A process for the preparation of percarboxylic acid which comprises reacting hydrogen peroxide and a water miscible aliphatic carboxylic acid between about 40° C. and 100° C. and at a pressure between about 20 and 100 mm of mercury in the presence of a catalytic amount of orthoboric or metaboric acid and a solvent capable of forming a heteroazeotrope with the water, and continuously eliminating the water which may have been introduced with the hydrogen peroxide as well as the water formed during the reaction by azeotropic distillation.

2. A process according to claim 1 in which the catalyst is used in a proportion of about 0.001 to 0.1 mole per mole of hydrogen peroxide.

3. A process according to claims 1 or 2 in which the solvent used as an azeotropic entrainer contains chlorine.

4. A process according to claims 1 or 2 in which cyclohexane is used as an azeotropic entrainer.

5. A process according to claims 1 or 2 in which the carboxylic acid is formic acid, acetic acid, proponic acid or butyric acid.

6. A process according to claim 1 in which the solution is an organic compound capable of forming a heteroazeotrope with the water and of reacting with the percarboxylic acid as it is formed in the reaction medium to oxidize the organic compound used as an azeotropic entrainer.

7. A process according to claim 6 where the azeotropic entrainer is an olefin.

8. A process according to claim 7 where the azeotropic entrainer is cyclohexene.

9. A process according to claim 7 where the azeotropic entrainer is allyl chloride.

* * * * *

UNITED STATES PATENT AND TRADEMARK OFFICE
CERTIFICATE OF CORRECTION

PATENT NO. : 4,338,260

DATED : July 6, 1982

INVENTOR(S) : Jean-Pierre Schirmann

It is certified that error appears in the above-identified patent and that said Letters Patent is hereby corrected as shown below:

In claim 1, line 5, change "100" to --760--.

Signed and Sealed this

Seventh Day of February, 1989

Attest:

DONALD J. QUIGG

*Attesting Officer*     *Commissioner of Patents and Trademarks*